US012638471B2

(12) United States Patent
Sujith et al.

(10) Patent No.: US 12,638,471 B2
(45) Date of Patent: May 26, 2026

(54) DEVICE AND METHOD TO DETERMINE A SWIM METRIC

(71) Applicants: Robert Bosch GmbH, Stuttgart (DE); Robert Bosch Engineering and Business Solutions Private Limited, Bangalore (IN)

(72) Inventors: Cherukuri Sujith, Bengaluru (IN); Sengottuvelan Senthilmurugan, Erode (IN)

(73) Assignees: Robert Bosch GmbH, Stuttgart (DE); Robert Bosch Engineering and Business Solutions Private Limited, Bangalore (IN)

( * ) Notice: Subject to any disclaimer, the term of this patent is extended or adjusted under 35 U.S.C. 154(b) by 705 days.

(21) Appl. No.: 17/754,407

(22) PCT Filed: Oct. 22, 2020

(86) PCT No.: PCT/EP2020/079714
§ 371 (c)(1),
(2) Date: Mar. 31, 2022

(87) PCT Pub. No.: WO2021/083779
PCT Pub. Date: May 6, 2021

(65) Prior Publication Data
US 2022/0341966 A1 Oct. 27, 2022

(30) Foreign Application Priority Data
Oct. 31, 2019 (IN) .............................. 201941044062

(51) Int. Cl.
*G01F 15/18* (2006.01)
*A61B 5/00* (2006.01)
(Continued)

(52) U.S. Cl.
CPC ............ *G01F 15/18* (2013.01); *A61B 5/7264* (2013.01); *A63B 71/0622* (2013.01); *G07C 1/22* (2013.01);
(Continued)

(58) Field of Classification Search
CPC ..... G01P 15/18; A61B 5/7264; A61B 5/1123; A63B 2220/17; A63B 2220/40; A63B 2244/02
See application file for complete search history.

(56) References Cited

U.S. PATENT DOCUMENTS

| | | | |
|---|---|---|---|
| 10,698,219 B1 * | 6/2020 | Eisenhardt | ......... A63B 24/0021 |
| 2003/0138763 A1 * | 7/2003 | Roncalez | ............... A63B 71/06 434/254 |

(Continued)

OTHER PUBLICATIONS

International Search Report corresponding to PCT Application No. PCT/EP2020/079714, mailed Jan. 29, 2021 (English language document) (4 pages).

(Continued)

*Primary Examiner* — Carl V Larsen
(74) *Attorney, Agent, or Firm* — Maginot, Moore & Beck LLP

(57) ABSTRACT

The device comprises at least one accelerometer, and a controller receiving input signals from the at least one accelerometer. The controller configured to filter stroke characteristics from the input signal using a filter module. The controller then applies a first statistical module on the filtered signal and obtains a first output signal. Due to the first statistical module, the first output signal is obtained, which is agnostic to type of swim stroke employed by the swimmer. The controller then determines the swim metric based on the first output signal and an adaptive threshold value. The swim metric is lap completion or lap count or turn event, during swimming by a swimmer. The device con-
(Continued)

sumes less power and also agnostic to swim styles and turn styles employed by swimmers.

8 Claims, 5 Drawing Sheets

(51) Int. Cl.
| | |
|---|---|
| *A63B 71/06* | (2006.01) |
| *G07C 1/22* | (2006.01) |
| *A61B 5/11* | (2006.01) |

(52) U.S. Cl.
CPC ..... *A61B 5/1123* (2013.01); *A63B 2071/0625* (2013.01); *A63B 2071/0663* (2013.01); *A63B 2220/17* (2013.01); *A63B 2220/40* (2013.01); *A63B 2220/836* (2013.01); *A63B 2244/20* (2013.01)

(56) References Cited

U.S. PATENT DOCUMENTS

| | | | | |
|---|---|---|---|---|
| 2007/0197938 | A1* | 8/2007 | Tyson ................... | A61B 5/1072 |
| | | | | 600/595 |
| 2008/0018532 | A1* | 1/2008 | Mackintosh ........... | A63B 71/06 |
| | | | | 342/357.57 |
| 2009/0221403 | A1* | 9/2009 | Chan ................... | A63B 24/0062 |
| | | | | 482/8 |
| 2010/0204952 | A1 | 8/2010 | Irlam et al. | |
| 2010/0210975 | A1* | 8/2010 | Anthony, III ........ | A61B 5/1123 |
| | | | | 600/595 |
| 2012/0019381 | A1* | 1/2012 | Yuen ...................... | G16H 20/30 |
| | | | | 340/539.26 |
| 2014/0277628 | A1* | 9/2014 | Nieminen .............. | A63B 71/06 |
| | | | | 700/91 |
| 2014/0278220 | A1 | 9/2014 | Yuen | |
| 2016/0084869 | A1* | 3/2016 | Yuen ........................ | G01P 3/44 |
| | | | | 73/510 |
| 2017/0188864 | A1* | 7/2017 | Drury ................ | A61B 5/02427 |
| 2018/0043210 | A1* | 2/2018 | Niehaus ................ | A61B 5/1118 |
| 2018/0056128 | A1* | 3/2018 | Narasimha Rao ... | G01C 22/006 |
| 2018/0368737 | A1* | 12/2018 | Bonomi .............. | A61B 5/7264 |
| 2019/0269968 | A1* | 9/2019 | Eisenhardt ......... | A63B 24/0003 |
| 2019/0374816 | A1* | 12/2019 | Yun ...................... | A61B 5/0205 |
| 2020/0054925 | A1* | 2/2020 | Rosamino .......... | A63B 57/0006 |
| 2022/0134182 | A1* | 5/2022 | Hughes ................... | G06F 1/163 |
| | | | | 482/8 |
| 2022/0161117 | A1* | 5/2022 | Jessop ................... | G16H 50/30 |

OTHER PUBLICATIONS

Lieske, Tobias et al: "System on Chip Generation for Multi-Sensor and Sensor Fusion Applications", 2017 International Conference on Embedded Computer Systems: Architectures, Modeling, and Simulation (Samos), IEEE, Jul. 17, 2017 (Jul. 17, 2017), pp. 20-29, XP033334839 [retrieved on Apr. 20, 2018] Section VI. A, Figure 9.

* cited by examiner

202

204

206

208

210

$t_1$ $t_2$ $t_3$ $t_4$ $t_5$ $t_6$

DEVICE AND METHOD TO DETERMINE A SWIM METRIC

This application is a 35 U.S.C. § 371 National Stage Application of PCT/EP2020/079714, filed on Oct. 22, 2020, which claims the benefit of priority to Serial No. IN 201941044062, filed on Oct. 31, 2019 in India, the disclosures of which are incorporated herein by reference in their entirety.

TECHNICAL FIELD

The present disclosure relates to a device and method to determine a swim metric of a swimmer, specifically a turn or lap count.

BACKGROUND

An amateur/professional swimmer uses wrist watch having Inertial Measurement Unit (IMU) sensors such as accelerometer(s) and gyroscope(s) and mostly magnetometer. Among these three sensors, accelerometer consumes very less power whereas magnetometer has high power consumption. The existing products uses high power consuming sensors such as magnetometer (to get heading direction) and gyroscope (to estimate orientation) for turn event detection. Also, the gyroscope based turn detectors requires 'swim style' information, which needs to be estimated with high computational cost. The already existing devices uses combination of IMU (accelerometer and gyroscope) and/or magnetometer for 'Turn detector/Lap counter'. The method employed comprises, Machine Learning (ML) on IMU signal which have high computational complexity, to derive feature vectors and apply ML on extracted features, or orientation estimation on IMU signal (mostly on gyroscope) is used for turn detection, which is not agnostic to swim styles and turn styles, i.e., turn detector algorithm requires 'swim style' classification, or change in direction heading based on magnetometer signal.

According to a prior art US2010204952, a motion analysis device for sports is disclosed. A portable wrist worn device for determining information about the movement of a human body when swimming is described. The device comprises a waterproof housing containing: an accelerometer operable to generate an acceleration signal; a processor operable to process the acceleration signal so as to generate one or more metrics relating to the movement of the human body; and a means for feedback of the one or more metrics to the user. The accelerometer may be operable to generate an acceleration signal along an axis parallel to the proximo-distal axis of the user's arm in use and/or the accelerometer may be operable to generate an acceleration signal along an axis parallel to the dorsal-palmar axis of the user's hand in use. The device may also be used in sports other than swimming.

BRIEF DESCRIPTION OF THE DRAWINGS

An embodiment of the disclosure is described with reference to the following accompanying drawings.

DETAILED DESCRIPTION

Figure 1:
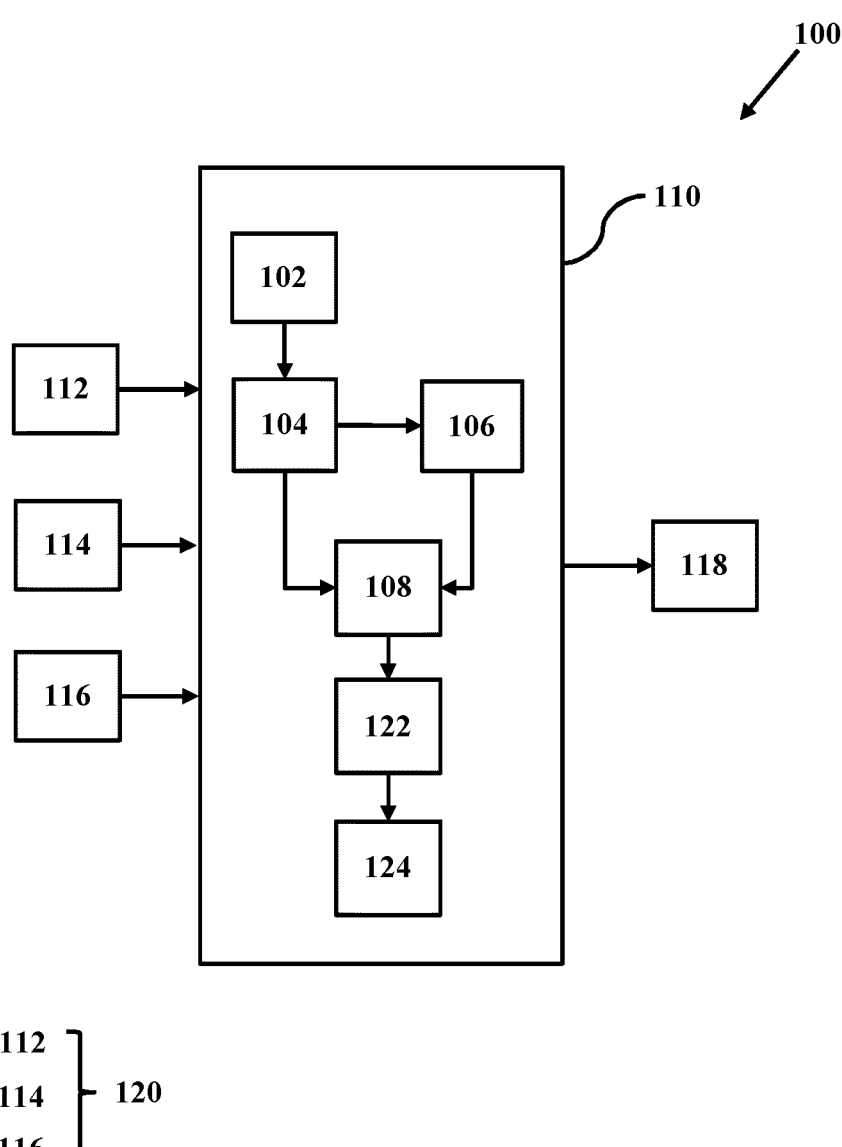
FIG. 1 illustrates a block diagram of a device to determine a swim metric, according to an embodiment of the present disclosure.

FIG. 1 illustrates a block diagram of a device to determine a swim metric, according to an embodiment of the present disclosure. The device 100 comprises at least one accelerometer 120, and a controller 110 to receive input signals from the at least one accelerometer 120. The controller 110 configured to filter stroke characteristics from the input signal using a filter module 102. The controller 110 then applies a first statistical module 104 on the filtered signal and obtains a first output signal. Due to the first statistical module 104, the first output signal is obtained which is agnostic to type of swim stroke employed by the swimmer. The first statistical output removes the stroke characteristics/signatures and enhances turn characteristics/signatures. The controller 110 then determines the swim metric based on the first output signal and an adaptive threshold value. The swim metric is lap completion or lap count or turn event, during swimming by a swimmer. The lap count is determined after the turn of the swimmer is successfully detected by the controller 110.

The controller 110 applies a second statistical module 106 to the first output signal and obtains a second output signal. The controller 110 then determines the adaptive threshold value as a multiple of the second output signal. The determined swim metric is validated by a validation module 108.

The validation is done by comparison of a duration of the turn characteristic with an empirically derived value. After the validation, the controller 110 stores the lap count and/or gives the output 118, such as display or sound. The filter module 102, the first statistical module 104, the second statistical module 106 and the validation module 108 are functions or set of instructions which are stored in a memory element (not shown) of the controller 110. The controller 110 invokes the modules as per the predetermined sequence to process the raw input signals received from the at least one accelerometer 120 to determine swim metric. Further, empirically derived value is also stored in the memory element.

The first statistical module 104 and the second statistical module 106 are based on standard deviation technique and moving average technique respectively, but not limited to the same. Other techniques known in the art are usable to obtain the similar or equivalent results.

In accordance to an embodiment of the present disclosure, the at least one accelerometer 120 comprises three accelerometers for three axis, i.e. a first accelerometer 112 for X-axis, a second accelerometer 114 for Y-axis and a third accelerometer 116 for Z-axis, respectively. The three accelerometers 112, 114, 116 are independently interfaced/connected to the controller 110. Alternatively the three accelerometers 112, 114 and 116 are integrated as a single unit, then interfaced to the controller 110.

In the case of three accelerometers 112, 114, 116, the controller 110 is capable of determining the swim metric by processing the raw input signals from at least one of the accelerometers 120. If the input signal of the first accelerometer 112 is processed first, then the same is used to determine the swim metric. In this case, the processed signals of the remaining accelerometers 114, 116 are optionally usable to further validate the swim metric.

Figure 2:
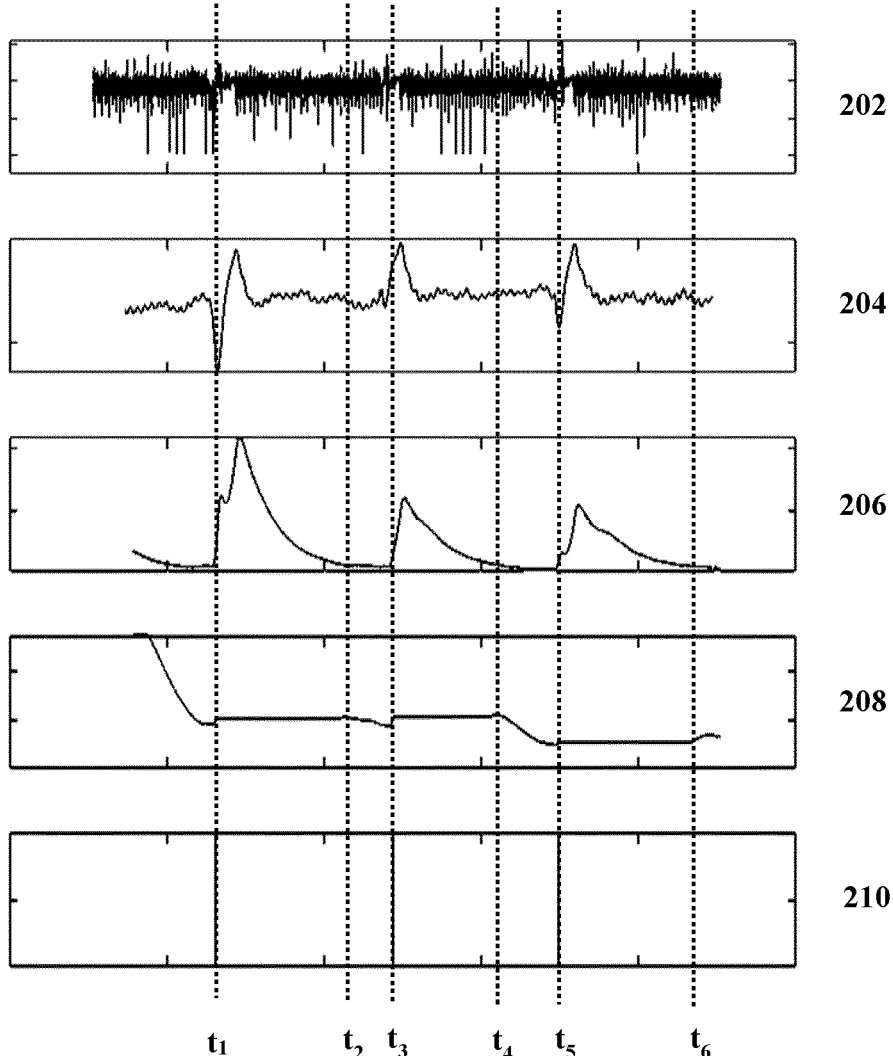
FIG. 2 illustrates waveforms depicting determination of the swim metric for a backstroke, according to an embodiment of the present disclosure.

FIG. 2 illustrates waveforms depicting determination of the swim metric for a backstroke, according to an embodiment of the present disclosure. The X-axis of the waveforms represents time and Y-axis represents voltage in respective suitable units. The first waveform 202 depicts the raw input signal from the at least one accelerometer 120. The raw accelerometer signal (of any axis) such as the first accelerometer 112 is fed to the controller 110 comprising of filter module 102. The filter module 102 such as but not limited to a low pass filter, an infinite impulse response (HR) filter, removes stroke characteristics/signatures and enhances turn characteristics/signatures. The filter module 102 is also referred to as enhancer module. The filtered signal obtained from the filter module 102 is depicted in second waveform 204. The filtered signal comprises peak, trough and both peak-trough at time instances $t_1$, $t_3$ and $t_5$.

The filtered signal is further processed by a cascade of statistical modules comprising the first statistical module 104 and the second statistical module 106. For example, the first statistical module 104 is an Exponential Weighted Standard Deviation (EWSD) filter or EW-Variance filter and the second statistical module 106 is an Exponential Weighted Moving Average (EWMA) filters, but not limited to the same. The parameter of the first statistical module 104 and the second statistical module 106 are empirically derived using swimming data collected from plurality of swimmers during multiple swimming sessions. The third waveform 206 is output of the first statistical module 104, and the fourth waveform 208 is the output of the second statistical module 106. As can be seen, in the third waveform 206, there is a start of a peak corresponding to start of variations in filtered signal at the time instances $t_1$, $t_3$ and $t_5$. The third waveform 206 shows variation only in one side in comparison to the second waveform 204 at the same time instances. Thus, irrespective of the variations detected in the filtered signal, the first output signal shows variations (peaks) in one side highlighting the turn characteristics. The first statistical module 104, makes the filtered signal to be agnostic of swim-styles and turn-styles performed by swimmers.

The fourth waveform 208 is an output from the second statistical module 106. The second statistical module 106 processes the first output signal obtained from the first statistical module 104. If the value of the second output signal, calculated by the second statistical module 106, exceeds the corresponding value of the first output signal, the controller 110 holds the value at the same level, until it becomes less than the value of the first output signal. This is shown between time instances $t_1$ and $t_2$, $t_1$ and $t_2$ and $t_5$ and $t_6$. At $t_1$, the second output signal (refer fourth waveform 208) is detected to be more than the corresponding value of the first output signal (refer third waveform 206) and is referred to as start time. The value is held till it becomes less than the corresponding value of the first output signal (refer third waveform 206), which occurs at time instance $t_2$, referred to as stop time. The variation in the second output signal is visible between time instances $t_2$ and $t_3$.

Based on the value of the second output signal, i.e. the fourth waveform 208, the adaptive threshold value is calculated. The adaptive threshold value is calculated as a multiple of the value of the second output signal, such as three times. The controller 110, detects the turns characteristics based on those values which exceeds the adaptive threshold value, and thus determines the turns, and in turn the swim metric. The first output signal which is style agnostic (both swim style and turn style) is processed along with the adaptive threshold value to determine the swim metric. The turn characteristics are segmented from the first output signal using the calculated/estimated adaptive threshold value. The detected swim metric are then validated using the validation module 108. The validation module 108 uses the temporal features (derived from first output signal) to output 'valid turn/lap' signal. The validation module 108 compares the duration of the turn characteristic by subtracting the start time and the stop time, with a standard empirically derived value. If matched, the determined turn characteristic is confirmed and updated in the memory element. A fifth waveform 210 shows the validation signal at time instances $t_1$, $t_3$ and $t_5$.

The output of the validation module 108 for at least one accelerometer 120 are fused together to give a final flag which is used for the swim metric, i.e. lap counting. The fusion is performed by a fusion module 122.

Figure 3:
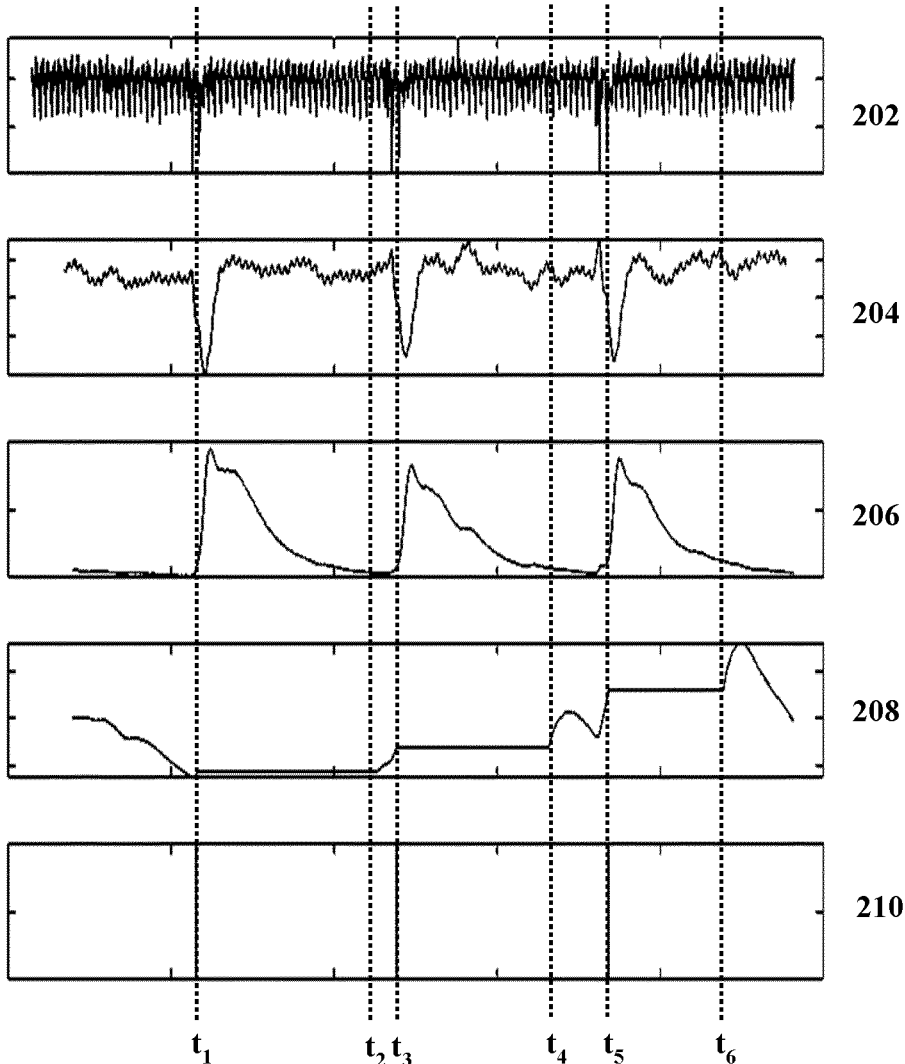
FIG. 3 illustrates waveforms depicting determination of the swim metric for a breaststroke, according to an embodiment of the present disclosure.

FIG. 3 illustrates waveforms depicting determination of the swim metric for a breaststroke, according to an embodiment of the present disclosure. The explanation is similar to the one given in FIG. 2, and avoided here for simplicity. The illustrated waveforms are for explanation purpose only, and must not be limited to the same. The waveforms may change based on the way of operation or surroundings.

Figure 4:
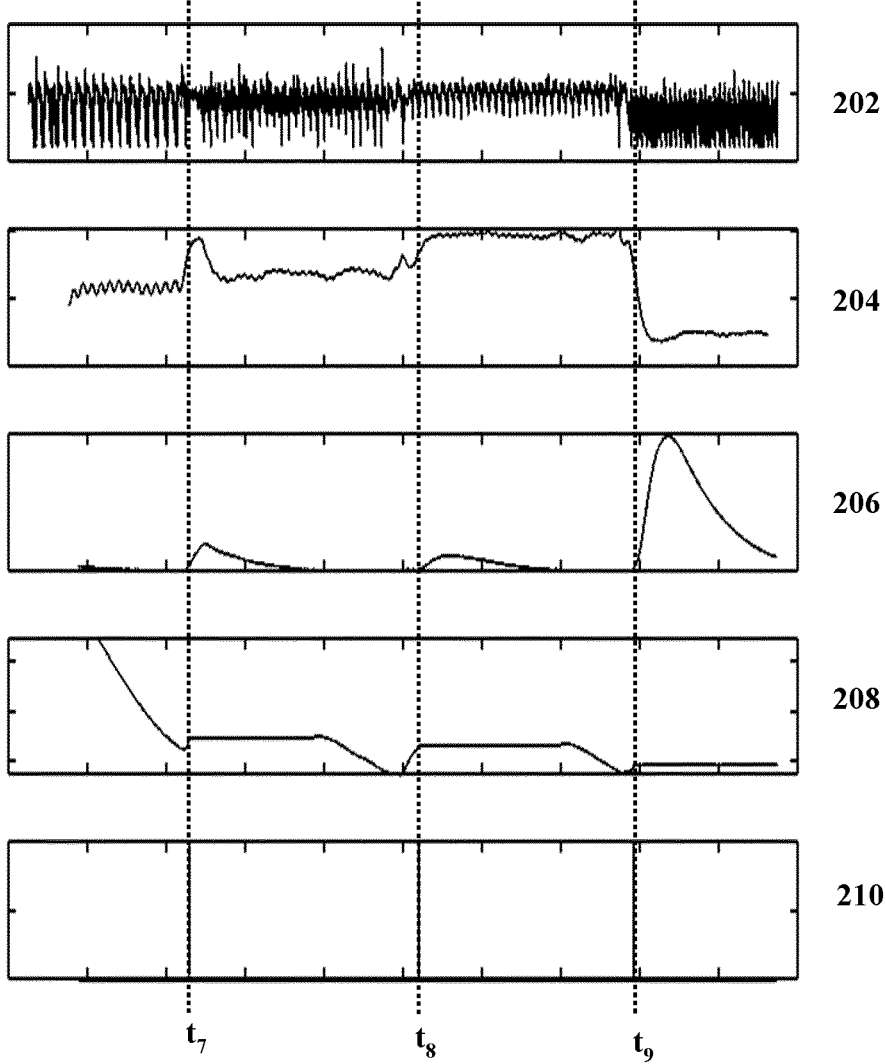
FIG. 4 illustrates waveforms depicting determination of the swim metric in a medley, according to an embodiment of the present disclosure.

FIG. 4 illustrates waveforms depicting determination of the swim metric in a medley, according to an embodiment of the present disclosure. The medley is combination of different stroke types such as backstroke, butterfly stroke, breast stroke and freestyle. Again, the explanation is avoided for simplicity. In the waveforms, till $t_1$, backstroke is performed, then breaststroke, followed by butterfly stroke and then freestyle. Irrespective of the type of stroke, the device 100 is able to detect the turn characteristic and determine the swim metric.

According to another embodiment of the present disclosure, the output of fusion module 122 (after fusion of the at least one accelerometer 120) is fed to a post processing module 124. The post processing module 124 takes two inputs, i.e. the output from the fusion module 122 and an output of a stroke counter module (not shown). Whenever the output of the fusion module 122 is TRUE, i.e. the flag is TRUE, the post processing module 124 checks a condition, and accordingly detects status of the swim metric, i.e. the validity of the determined lap. The condition comprises if the number of strokes in the completed lap is more than a threshold limit, then the determination of the swim metric is true, else the swim metric determined is false. If false, the swim metric determined is nullified and not recorded. The threshold limit corresponds to the average stroke counts per lap derived adaptively during each swim session or empirically calculated and stored in the memory element of the controller 110. For example, if the number of strokes completed is more than 75% of the threshold limit, then the determined swim metric, i.e. the lap is valid and recorded else it is discarded.

Figure 5:
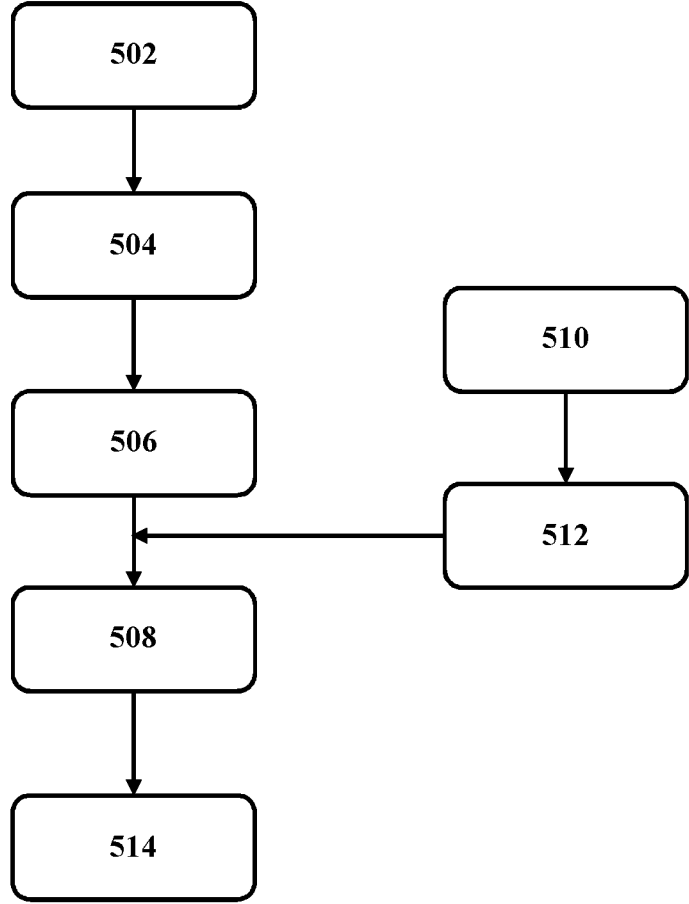
FIG. 5 illustrates a method for determining the swim metric, according to the present disclosure.

FIG. 5 illustrates a method for determining a swim metric, according to the present disclosure. The method comprises the steps of, a step 502 comprising, receiving at least one input signal from the at least one accelerometer 120. A step 504 comprises filtering stroke characteristics from the at least one input signal received in step 502. A step 506 comprises applying the first statistical module 104 on the filtered signal and obtaining the first output signal. Due to the use of first statistical module 104, the first output signal is agnostic of swim type and turn type employed by the swimmer. A step 508 comprises determining the swim metric based on the first output signal and the adaptive threshold value. The step 506 of obtaining the first output signal is followed by a step 510 and a step 512. The step 510 comprises applying a second statistical module 106 to the first output signal and obtaining the second output signal. The step 512 comprises calculating the adaptive threshold value as the multiple of the second output signal.

The method further comprises a step 514 comprising validating the determined swim metric by comparing of the duration of the determined swim metric with the empirically derived value. The step 514 is performed after the step 508. The steps of applying the first statistical module 104 and the second statistical module 106 are based on methods of standard deviation and moving average, respectively, but not restricted to the same.

Further, the step of receiving at least one input signal from the at least one accelerometer 120 comprises receiving three input signals from three accelerometers 112, 114, 116 corresponding to three axis. The three accelerometers 112, 114, 116 are any one of independently interfaced with the controller 110 and integrated as a single unit and then interfaced with the controller 110.

According to an embodiment of the present disclosure, the device 100 provides accelerometer 120 based lap counter for swim tracking wearable solution. The device 100 consumes less power and also agnostic to swim styles and turn styles employed by swimmers. The power consumption of the at least one accelerometer 120 is very less as compared to gyroscope and magnetometer sensors. Further, the controller 110 uses less computational complexity of filters and/or modules or signal processing as compared to existing solutions. The device 100 is any one of a fitness bands/watch or in general wearable electronic devices.

It should be understood that embodiments explained in the description above are only illustrative and do not limit the scope of this disclosure. Many such embodiments and other modifications and changes in the embodiment explained in the description are envisaged. The scope of the disclosure is only limited by the scope of the claims.

We claim:

1. A device for determining a swim metric, the device comprising:

a three-axis accelerometer configured to measure three-axis inputs signals; and a controller that receives the three-axis input signals from the three-axis accelerometer, the controller being configured to:

generate filtered input signals by filtering a first axis of the three-axis input signals to remove stroke characteristics from the three-axis input signals, generate a first output signal that is agnostic to a type of swim stroke employed by a swimmer by applying a first statistical module to the filtered first axis of the three-axis input signals;

generate a second output signal by applying a second statistical module to the first output signal;

calculate an adaptive threshold value as a multiple of the second output signal;

determine the swim metric by (i) comparing the first output signal with the adaptive threshold value, (ii) determining turn characteristics based on values of the first output signal that exceed the adaptive threshold value, and (iii) determining the swim metric based on the turn characteristics;

validate the swim metric by processing a second axis and a third axis of the three-axis input signals; and operate a display device or sound device to output depending on the swim metric.

2. The device as claimed in claim 1, wherein the determined swim metric is validated by comparing a duration of a turn characteristic in the first output signal with an empirically derived value.

3. The device as claimed in claim 1, wherein the first statistical module and the second statistical module are based on a standard deviation technique and a moving average technique, respectively.

4. The device as claimed in claim 1, wherein:

the three-axis accelerometer comprises three accelerometers; and the three accelerometers are one of (i) independently interfaced with the controller and (ii) integrated as a single unit that is interfaced with the controller.

5. A method for determining a swim metric, the method being executed by a controller, the method comprising:

receiving three-axis input signals from a three-axis accelerometer;

generating filtered input signals filtering a first axis of the three-axis input signals to remove stroke characteristics from the three-axis input signals;

generating a first output signal that is agnostic to a type of swim stroke employed by a swimmer by applying a first statistical module to the filtered first axis of the three-axis input signals;

generate a second output signal by applying a second statistical module to the first output signal;

calculating an adaptive threshold value as a multiple of the second output signal;

determining the swim metric by (i) comparing the first output signal with the adaptive threshold value, (ii) determining turn characteristics based on values of first output signal that exceed the adaptive threshold value, and (iii) determining the swim metric based on the turn characteristics;

validating the swim metric by processing a second axis and a third axis of the three-axis input signals; and operating a display device or sound device to output depending on the swim metric.

6. The method as claimed in claim 5 further comprising: validating the determined swim metric by comparing a duration of a turn characteristic in the first output signal with an empirically derived value.

7. The method as claimed in claim 5, wherein the applying the first statistical module and the applying the second statistical module are based on methods of standard deviation and moving average, respectively.

8. The method as claimed in claim 5, wherein:

the receiving the three-axis input signals from the three-axis accelerometer comprises receiving three input signals from three accelerometers corresponding to three axes; and the three accelerometers are one of (i) independently interfaced with the controller and (ii) integrated as a single unit that is interfaced with the controller.

* * * * *